(12) United States Patent
Arnold et al.

(10) Patent No.: US 8,795,975 B2
(45) Date of Patent: Aug. 5, 2014

(54) METHODS AND COMPOSITIONS FOR DIAGNOSIS AND RISK PREDICTION IN HEART FAILURE

(75) Inventors: William D. Arnold, San Diego, CA (US); Christelle Jost, San Diego, CA (US); Brian Noland, Temecula, CA (US); Jonathan Gary, San Diego, CA (US); Joseph Buechler, Carlsbad, CA (US); Vance Wong, Cardiff, CA (US); Scott Harold Rongey, San Diego, CA (US); Uday Kumar Veeramallu, San Diego, CA (US); Kelline Marie Rodems, Oceanside, CA (US)

(73) Assignee: Alere San Diego, Inc., San Diego, CA (US)

( * ) Notice: Subject to any disclaimer, the term of this patent is extended or adjusted under 35 U.S.C. 154(b) by 0 days.

(21) Appl. No.: 13/990,393

(22) PCT Filed: Nov. 25, 2011

(86) PCT No.: PCT/US2011/062159
§ 371 (c)(1),
(2), (4) Date: Aug. 13, 2013

(87) PCT Pub. No.: WO2012/074888
PCT Pub. Date: Jun. 7, 2012

(65) Prior Publication Data
US 2014/0147867 A1 May 29, 2014

Related U.S. Application Data

(60) Provisional application No. 61/417,851, filed on Nov. 29, 2010, provisional application No. 61/437,609, filed on Jan. 29, 2011.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/130.1; 422/430; 530/300; 530/350

(58) Field of Classification Search
None
See application file for complete search history.

(56) References Cited

U.S. PATENT DOCUMENTS

| 2002/0081607 | A1 | 6/2002 | Ruben et al. |
| 2004/0265926 | A1 | 12/2004 | Ng |
| 2006/0019272 | A1 | 1/2006 | Geraci et al. |

OTHER PUBLICATIONS

International Search Report and Written Opinion issued May 25, 2012 in PCT/US2011/062159.

*Primary Examiner* — Lisa Cook
(74) *Attorney, Agent, or Firm* — Michael A. Whittaker; Acuity Law Group, P.C.

(57) ABSTRACT

The present invention relates in part to diagnosing the occurrence of heart failure, particularly in subjects who exhibit a normal body fluid level of a natriuretic peptide. The present invention further relates in part to assigning an outcome risk (e.g., worsening cardiac function or a mortality risk, a risk of rehospitalization) to a subject. The methods comprise performing one or more assays that detect one or more biomarkers selected from the group consisting of WAP4C, ESAM, LTBR, Mesothelin, and Syndecan-1 performed on a body fluid sample obtained from a subject, and assigning diagnosis or risk based, at least in part, on the result(s) obtained thereby.

26 Claims, No Drawings

METHODS AND COMPOSITIONS FOR DIAGNOSIS AND RISK PREDICTION IN HEART FAILURE

The present invention is filed under 35 U.S.C. §371 as the U.S. national phase of International Application No. PCT/US2011/062159, filed Nov. 29, 2011, which designated the U.S. and claims priority of U.S. Provisional Patent Application No. 61/417,851 filed Nov. 29, 2010; and of U.S. Provisional Patent Application No. 61/437,609 filed Jan. 29, 2011, each of which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on May 29, 2013, is named ALERE001US_SeqListing_txt.txt and is 29,696 bytes in size.

FIELD OF THE INVENTION

The present invention relates to methods and compositions for monitoring cardiorenal syndrome, and the heart failure and renal dysfunction underlying the cardiorenal syndrome.

BACKGROUND OF THE INVENTION

The following discussion of the background of the invention is merely provided to aid the reader in understanding the invention and is not admitted to describe or constitute prior art to the present invention.

Congestive heart failure (CHF) is a fatal disease with a 5-year mortality rate that rivals the most deadly malignancies. For example, in the Framingham Heart Study, median survival after the onset of heart failure was 1.7 years in men and 3.2 years in women. Overall, 1-year and 5-year survival rates were 57% and 25% in men and 64% and 38% in women, respectively. Moreover, a person age 40 or older has a one-in-five lifetime chance of developing congestive heart failure. Heart failure typically develops after other conditions have damaged the heart. Coronary artery disease, and in particular myocardial infarction, is the most common form of heart disease and the most common cause of heart failure.

The appropriate treatments given to patients suffering from heart failure are diverse. For example, diuretics are often given to reduce the increased fluid load characteristic of heart failure; Angiotensin-converting enzyme (ACE) inhibitors are a class of vasodilator used to lower blood pressure, improve blood flow and decrease the workload on the heart; Angiotensin II receptor blockers (ARBs) have many of the same benefits as ACE inhibitors; and Beta blockers may reduce signs and symptoms of heart failure and improve heart function.

In recent years, natriuretic peptide measurement has dramatically changed the diagnosis and management of cardiac diseases, including heart failure and the acute coronary syndromes. In particular, B-type natriuretic peptide (BNP, human precursor Swiss-Prot P16860), various related polypeptides arising from the common precursor proBNP (such as NT-proBNP), and proBNP itself have been used to diagnose heart failure, determine its severity, and estimate prognosis. In addition, BNP and its related polypeptides have been demonstrated to provide diagnostic and prognostic information in unstable angina, non-ST-elevation myocardial infarction, and ST-elevation myocardial infarction.

BNP and its related peptides are correlated with other measures of cardiac status such as New York Heart Association classification. However, many patients with chronic stable or asymptomatic heart failure will have natriuretic peptide levels in the normal diagnostic range (e.g., BNP levels less than about 100 pg/mL; NT-proBNP levels less than about 400 pg/mL). There is a trade-off in selecting diagnostic cutoff levels for these markers, because lowering the cutoff decreases the false-negative rate (i.e., increased sensitivity and fewer missed diagnoses) but increases the false-positive rate (i.e., decreased specificity and more incorrect diagnoses).

There remains a need in the art for markers which can be used for diagnosis and risk stratification of patients having or suspected of having congestive heart failure.

BRIEF SUMMARY OF THE INVENTION

It is an object of the invention to provide methods and compositions for diagnosis, prognosis, and determination of treatment regimens in subjects suffering from, or being evaluated for, heart failure. In various aspects, the present invention provides methods for diagnosis of heart failure, assessing risk of worsening heart failure; methods for assigning risk of mortality in the context of heart failure, methods of monitoring heart failure; and various devices and kits adapted to perform such methods.

In a first aspect, the present invention relates to methods for diagnosing heart failure. These methods comprise performing an assay method configured to detect performing one or more assays selected from the group consisting of an assay that detects WAP four-disulfide core domain protein 2 (also known as "WAP4C" and "HE4"), an assay that detects ESAM, an assay that detects LTBR, an assay that detects Mesothelin, an assay that detects Syndecan-1, an assay that detects TROY, and an assay that detects PIGR on a body fluid sample obtained from a subject, thereby providing one or more assay result(s); and assigning a diagnosis that the subject has or does not have heart failure based on the assay result(s) obtained.

In a related aspect, the present invention relates to methods for risk stratification—that is, assigning an outcome risk—to a subject. These methods comprise performing one or more assays selected from the group consisting of an assay that detects WAP4C, an assay that detects ESAM, an assay that detects LTBR, an assay that detects Mesothelin, an assay that detects Syndecan-1, an assay that detects TROY, and an assay that detects PIGR on a body fluid sample obtained from a subject, thereby providing one or more assay result(s); and assigning an outcome risk based on the assay result(s) obtained.

In certain embodiments described herein, each assay result is compared to a corresponding baseline (i.e., a diagnostic or prognostic "threshold") level which is considered indicative of a "positive" or "negative" result. A variety of methods may be used by the skilled artisan to arrive at a desired baseline. In certain preferred embodiments, the baseline assay result is determined from an earlier assay result obtained from the same subject. That is, the change in a biomarker concentration may be observed over time, and an increased concentration provides an indication of the onset of, or worsening, heart failure in the subject.

In alternative embodiments, the baseline assay result is determined from a population of subjects. In the case of the use of the markers of the present invention for diagnosis, the population may contain some subjects which suffer from heart failure, and some which do not; in the case of the use of the markers of the present invention for use for prognosis, the population may contain some subjects which suffer from some outcome (e.g., cardiovascular mortality; worsening heart failure; improving heart failure, etc.), and some which do not. As described hereinafter, a threshold is selected which provides an acceptable level of specificity and sensitivity in separating the population into a "first" subpopulation exhibiting a particular characteristic (e.g., having an increased risk of worsening heart failure) relative to the remaining "second" subpopulation that does not exhibit the characteristic. As discussed herein, a preferred threshold value separates this first and second population by one or more of the following measures of test accuracy:

an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less.

at least 75% sensitivity, combined with at least 75% specificity;

a ROC curve area of at least 0.6, more preferably 0.7, still more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20; or a negative likelihood ratio (calculated as (1-sensitivity)/specificity) of less than or equal to 0.3, more preferably less than or equal to 0.2, and most preferably less than or equal to 0.1. The term "about" in this context refers to +/−5% of a given measurement.

The present risk stratification methods preferably assign a "near-term" risk of worsening heart failure or cardiovascular mortality. By "near term" is meant within 30 days. As described hereinafter, the methods preferably assign a risk within 7 days, more preferably within 5 days, and still more preferably within 3 days.

Preferred assay methods comprise performing an immunoassay that detects a marker of interest. Antibodies for use in such assays will specifically bind the marker of interest, and may optionally also bind one or more polypeptides that are "related" thereto, as described hereinafter with regard to related markers. Such immunoassays may comprise contacting said body fluid sample with a solid phase antibody that detects the marker, and detecting binding to that antibody, although assay formats that do not require the use of a solid phase are known in the art. While the present invention is generally described in terms of immunoassays, other binding entities (e.g., aptamers) which are not based on an immunoglobulin scaffold may be used in lieu of antibodies in such methods. Preferably, the body fluid sample is selected from the group consisting of urine, blood, serum, and plasma.

It is not intended that a diagnosis or prognosis be assigned based exclusively on the assay result(s). Rather, the skilled artisan will understand that a diagnosis, prognosis, monitoring, etc., can also consider numerous additional clinical variables as described hereinafter, provided that the assay results are variables considered during the diagnostic process; that is, the assay result(s) are used to increase or decrease the probability that the subject under study suffers from heart failure. As described in additional detail hereinafter, assays that detect various markers (both subject-derived and physical characteristics) may be combined, including assays that detect various natriuretic peptides such as BNP, NT-proBNP, and proBNP; markers related to inflammation such as myeloperoxidase, soluble FLT-1, C-reactive protein, and placental growth factor; markers related to cardiac damage such as cardiac troponins and CK-MB; markers of renal damage such as serum creatinine, creatinine clearance rates, cystatin C, and glomerular filtration rates; and variables such as urine output levels, age, the presence or absence of various cardiovascular risk factors such as diabetes, hypertension, body mass, smoking status; etc.

In certain embodiments, the methods comprise performing a plurality of assays (e.g., 2, 3, 4 or more) selected from the group consisting of an assay that detects WAP4C, an assay that detects ESAM, an assay that detects LTBR, an assay that detects Mesothelin, an assay that detects Syndecan-1, an assay that detects TROY, and an assay that detects PIGR. In methods where multiple assays are performed on body fluids, the various assays can be performed on the same or different body fluid samples. For example, ESAM may be measured in a urine sample and LTBR may be measured in a plasma sample; or ESAM may be measured in a plasma sample and LTBR measured in a different plasma sample.

In still another aspect, the present invention relates to methods for monitoring cardiovascular disease in a patient. These methods comprise performing one or more assays selected from the group consisting of an assay that detects WAP4C, an assay that detects ESAM, an assay that detects LTBR, an assay that detects Mesothelin, an assay that detects Syndecan-1, an assay that detects TROY, and an assay that detects PIGR on serially collected body fluid samples obtained from a subject, thereby providing one or more assay result(s). A worsening cardiovascular disease status may be assigned to the patient if the assay result(s) are increasing with time. In the alternative, an improving cardiovascular disease status may be assigned to the patient if the assay result(s) are decreasing with time.

In certain embodiments, reagents for performing such assays are provided in an assay device, and such assay devices may be included in such a kit. Preferred reagents comprise one or more solid phase antibodies, the solid phase antibody comprising antibody that detects the intended target(s) bound to a solid support. In the case of sandwich immunoassays, such reagents can also include one or more detectably labeled antibodies, the detectably labeled antibody comprising antibody that detects the intended target(s) bound to a detectable label. Additional optional elements that may be provided as part of an assay device are described hereinafter.

DETAILED DESCRIPTION OF THE INVENTION

The present invention relates to methods and compositions for diagnosis, prognosis, and determination of treatment regimens in subjects suffering from congestive heart failure.

As described herein, the present invention relates in part to diagnosing the occurrence of heart failure, particularly in subjects who exhibit a normal body fluid level of a natriuretic peptide. The present invention further relates in part to assigning an outcome risk (e.g., worsening cardiac function or a mortality risk) to a subject based, at least in part, on the result(s) obtained from one or more assays that detect one or more biomarkers selected from the group consisting of WAP4C, ESAM, LTBR, TROY, Mesothelin, and Syndecan-1 performed on a body fluid sample obtained from a subject.

If the sample tested is obtained from the subject at a time t, the phrase "short term risk" refers to a 7-day (168 hour) period measured from time t. Thus, the risk is a likelihood that the subject will suffer from deterioration of one or more measures of cardiac function, or will die, in a window beginning at time t and ending 168 hours later. Suitable measures of cardiac function include one or more of: dyspnea (at rest or exertional), orthopnea, pulmonary edema, SaO$_2$ level, dizziness or syncope, chest pain, systolic blood pressure, hypoperfusion, edema, compensation status (that is, a change from compensated to decompensated, or vice versa), end-diastolic function, end-systolic function, ventricular filling, flow across the mitral valve, left ventricular ejection fraction (LVEF), results of stress testing, results of an imaging study such as a cardiac CT, ultrasound, or MRI, NYHA or American College of Cardiology heart failure classification, etc. These characteristics, and methods for their assessment, are well known in the art. See, e.g., *Harrison's Principles of Internal Medicine*, 16$^{th}$ ed., McGraw-Hill, 2005, pages 1361-1377, which is hereby incorporated by reference in its entirety. This list is not meant to be limiting.

More preferably, the risk is a likelihood that the subject will suffer from deterioration of one or more of these measures of cardiac function, or will die, in a 96 hour window beginning at time t, and most preferably the risk is a likelihood that the subject will suffer from deterioration of one or more of these measures of cardiac function, or a likelihood that the subject will die, in a window of between 48 and 84 hours beginning at time t. The term "deterioration" as used herein refers to a worsening change in a parameter at a later time, relative to a measure of the same parameter earlier in the same subject, and is the opposite of "improvement." For example, "deterioration in cardiac function" as used herein refers to a later change in the subject from an asymptomatic state to NYHA heart failure class I or greater; worsening LVEF, etc.

The terms "marker" and "biomarker" as used herein refers to proteins, polypeptides, glycoproteins, proteoglycans, lipids, lipoproteins, glycolipids, phospholipids, nucleic acids, carbohydrates, etc. or small molecules to be used as targets for screening test samples obtained from subjects. "Proteins or polypeptides" used as markers in the present invention are contemplated to include any fragments thereof, in particular, immunologically detectable fragments. Markers can also include clinical "scores" such as a pre-test probability assignment, a pulmonary hypertension "Daniel" score, an NIH stroke score, a Sepsis Score of Elebute and Stoner, a Duke Criteria for Infective Endocarditis, a Mannheim Peritonitis Index, an "Apache" score, etc.

The sequence of the 108 amino acid BNP precursor pro-BNP (BNP$_{1-108}$) is as follows, with mature BNP (BNP$_{77-108}$) underlined:

```
                                                    (SEQ ID NO: 1).
HPLGSPGSAS DLETSGLQEQ RNHLQGKLSE LQVEQTSLEP LQESPRPTGV      50

WKSREVATEG IRGHRKMVLY TLRAPRSPKM VQGSGCFGRK MDRISSSSGL     100

GCKVLRRH                                                  108
```

BNP$_{1-108}$ is synthesized as a larger precursor pre-pro-BNP having the following sequence (with the "pre" sequence shown in bold):

```
                                                    (SEQ ID NO: 2).
MDPQTAPSRA LLLLLFLHLA FLGGRSHPLG SPGSASDLET SGLQEQRNHL      50

QGKLSELQVE QTSLEPLQES PRPTGVWKSR EVATEGIRGH RKMVLYTLRA     100

PRSPKMVQGS GCFGRKMDRI SSSSGLGCKV LRRH                     134
```

While a mature protein (e.g., BNP) itself may be used as a marker in the present invention, various related markers that may be measured either as surrogates for a mature protein of interest or as markers in and of themselves. Thus, BNP-related polypeptides prepro-BNP, BNP$_{1-108}$ and BNP$_{1-76}$ may replace BNP as a heart failure marker. "Related markers" to each of the markers described herein may be identified and used in an analogous fashion to that described above for BNP.

As used herein, the term "ESAM" or "Endothelial cell-selective adhesion molecule" refers to one or polypeptides present in a biological sample that are derived from the Endothelial cell-selective adhesion molecule precursor (Swiss-Prot Q96AP7 (SEQ ID NO: 3)).

```
           10         20         30         40         50         60
    MISLPGPLVT NLLRFLFLGL SALAPPSRAQ LQLHLPANRL QAVEGGEVVL PAWYTLHGEV 70         80         90        100        110        120
    SSSQPWEVPF VMWFFKQKEK EDQVLSYING VTTSKPGVSL VYSMPSRNLS LRLEGLQEKD 130        140        150        160        170        180
    SGPYSCSVNV QDKQGKSRGH SIKTLELNVL VPPAPPSCRL QGVPHVGANV TLSCQSPRSK 190        200        210        220        230        240
    PAVQYQWDRQ LPSFQTFFAP ALDVIRGSLS LTNLSSSMAG VYVCKAHNEV GTAQCNVTLE 250        260        270        280        290        300
```

-continued

```
VSTGPGAAVV AGAVVGTLVG LGLLAGLVLL YHRRGKALEE PANDIKEDAI APRTLPWPKS 310        320        330        340        350        360
SDTISKNGTL SSVTSARALR PPHGPPRPGA LTPTPSLSSQ ALPSPRLPT  TDGAHPQPISP 370        380        390
IPGGVSSSGL SRMGAVPVMV PAQSQAGSLV
```

Most preferably, an ESAM assay detects one or more soluble forms of ESAM. ESAM is a single-pass type I membrane protein having a large extracellular domain, most or all of which are present in soluble forms of ESAM generated either through an alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in ESAM:

| Residues | Length | Domain ID |
|---|---|---|
| 1-29 | 29 | signal sequence |
| 30-390 | 361 | ESAM |
| 30-248 | 219 | extracellular |
| 249-269 | 21 | transmembrane |
| 270-390 | 121 | cytoplasmic |

As used herein, the term "LTBR" or "Tumor necrosis factor receptor superfamily member 3" refers to one or polypeptides present in a biological sample that are derived from the LTBR precursor (Swiss-Prot P36941 (SEQ ID NO: 4)).

```
        10         20         30         40         50         60
MLLPWATSAP GLAWGPLVLG LFGLLAASQP QAVPPYASEN QTCRDQEKEY YEPQHRICCS 70         80         90        100        110        120
RCPPGTYVSA KCSRIRDTVC ATCAENSYNE HWNYLTICQL CRPCDPVMGL EEIAPCTSKR 130        140        150        160        170        180
KTQCRCQPGM FCAAWALECT HCELLSDCPP GTEAELKDEV GKGNNHCVPC KAGHFQNTSS 190        200        210        220        230        240
PSARCQPHTR CENQGLVEAA PGTAQSDTTC KNPLEPLPPE MSGTMLMLAV LLPLAFFLLL 250        260        270        280        290        300
ATVFSCIWKS HPSLCRKLGS LLKRRPQGEG PNPVAGSWEP PKAHPYFPDL VQPLLPISGD 310        320        330        340        350        360
VSPVSTGLPA APVLEAGVPQ QQSPLDLTRE PQLEPGEQSQ VAHGTNGIHV TGGSMTITGN 370        380        390        400        410        420
IYIYNGPVLG GPPGPGDLPA TPEPPYPIPE EGDPGPPGLS TPHQEDGKAW HLAETEHCGA

430
TPSNRGPRNQ FITHD
```

Most preferably, an LTBR assay detects one or more soluble forms of LTBR. LTBR is a single-pass type I membrane protein having a large extracellular domain, most or all of which is present in soluble forms of LTBR generated either through an alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in LTBR:

| Residues | Length | Domain ID |
|---|---|---|
| 1-30 | 30 | signal sequence |
| 31-435 | 405 | LTBR |
| 31-227 | 197 | extracellular |
| 228-248 | 21 | transmembrane |
| 249-435 | 187 | cytoplasmic |

As used herein, the term "Mesothelin" refers to one or more polypeptides present in a biological sample that are derived from the Mesothelin precursor (Swiss-Prot Q13421 (SEQ ID NO: 5)).

```
        10         20         30         40         50         60
MALPTARPLL GSCGTPALGS LLFLLFSLGW VQPSRTLAGE TGQEAAPLDG VLANPPNISS 70         80         90        100        110        120
LSPRQLLGFP CAEVSGLSTE RVRELAVALA QKNVKLSTEQ LRCLAHRLSE PPEDLDALPL 130        140        150        160        170        180
```

-continued

```
DLLLFLNPDA FSGPQACTRF FSRITKANVD LLPRGAPERQ RLLPAALACW GVRGSLLSEA 190        200        210        220        230        240
DVRALGGLAC DLPGRFVAES AEVLLPRLVS CPGPLDQDQQ EAARAALQGG GPPYGPPSTW 250        260        270        280        290        300
SVSTMDALRG LLPVLGQPII RSIPQGIVAA WRQRSSRDPS WRQPERTILR PRFRREVEKT 310        320        330        340        350        360
ACPSGKKARE IDESLIFYKK WELEACVDAA LLATQMDRVN AIPFTYEQLD VLKHKLDELY 370        380        390        400        410        420
PQGYPESVIQ HLGYLFLKMS PEDIRKWNVT SLETLKALLE VNKGHEMSPQ APRRPLPQVA 430        440        450        460        470        480
TLIDRFVKGR GQLDKDTLDT LTAFYPGYLC SLSPEELSSV PPSSIWAVRP QDLDTCDPRQ 490        500        510        520        530        540
LDVLYPKARL AFQNMNGSEY FVKIQSFLGG APTEDLKALS QQNVSMDLAT FMKLRTDAVL 550        560        570        580        590        600
PLTVAEVQKL LGPHVEGLKA EERHRPVRDW ILRQRQDDLD TLGLGLQGGI PNGYLVLDLS 610        620        630
MQEALSGTPC LLGPGPVLTV LALLLASTLA
```

Most preferably, a Mesothelin assay detects one or more soluble forms of Mesothelin. Mesothelin is a GPI-linked membrane protein having a signal sequence which is cleaved off and replaced with a glycophospholipid membrane anchor during expression of the polypeptide. The following domains have been identified in Mesothelin:

| Residues | Length | Domain ID |
|---|---|---|
| 1-36 | 36 | signal sequence |
| 37-606 | 570 | Mesothelin |
| 37-286 | 250 | Megakaryocyte-potentiating factor |
| 296-606 | 311 | Mesothelin, cleaved form |
| 607-630 | 24 | propeptide |
| 406-416 | 11 | Missing in soluble variant |
| 601-630 | 30 | Replaced in soluble variant with |

(SEQ ID NO: 6)
VQGGRGGQARAGGRAGGVEVGALSHPSLCRGPLGDALPPRTWTCSHRPGTA

PSLHPGLRAPLPC

As used herein, the term "Syndecan-1" refers to one or more polypeptides present in a biological sample that are derived from the Syndecan-1 precursor (Swiss-Prot P18827 (SEQ ID NO: 7)).

Most preferably, a Syndecan-1 assay detects one or more soluble forms of Syndecan-1. Syndecan-1 is a single-pass type I membrane protein having a large extracellular domain, most or all of which is present in soluble forms of Syndecan-1 generated either through an alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Syndecan-1:

| Residues | Length | Domain ID |
|---|---|---|
| 1-22 | 22 | signal sequence |
| 23-310 | 405 | Syndecan-1 |
| 23-254 | 232 | extracellular |
| 255-275 | 21 | transmembrane |
| 276-310 | 35 | cytoplasmic |

As used herein, the term "TROY" or "Tumor necrosis factor receptor superfamily member 19") refers to one or more polypeptides present in a biological sample that are derived from the TROY precursor (Swiss-Prot Q9NS68 (SEQ ID NO: 8)).

```
        10         20         30         40         50         60
MRRAALWLWL CALALSLQPA LPQIVATNLP PEDQDGSGD DSDNFSGSGAG ALQDITLSQQ 70         80         90        100        110        120
TPSTWKDTQL LTAIPTSPEP TGLEATAAST STLPAGEGPK EGEAVVLPEV EPGLTAREQE 130        140        150        160        170        180
ATPRPRETTQ LPTTHLASTT TATTAQEPAT SHPHRDMQPG HHETSTPAGP SQADLHTPHT 190        200        210        220        230        240
EDGGPSATER AAEDGASSQL PAAEGSGEQD FTFETSGENT AVVAVEPDRR NQSPVDQGAT 250        260        270        280        290        300
GASQGLLDRK EVLGGVIAGG LVGLIFAVCL VGFMLYRMKK KDEGSYSLEE PKQANGGAYQ

310
KPTKQEEFYA
```

```
        10         20         30         40         50         60
MRRAALWLWL CALALSLQPA LPQIVATNLP PEDQDGSGDD SDNFSGSGAG ALQDITLSQQ 70         80         90        100        110        120
TPSTWKDTQL LTAIPTSPEP TGLEATAAST STLPAGEGPK EGEAVVLPEV EPGLTAREQE 130        140        150        160        170        180
ATPRPRETTQ LPTTHLASTT TATTAQEPAT SHPHRDMQPG HHETSTPAGP SQADLHTPHT 190        200        210        220        230        240
EDGGPSATER AAEDGASSQL PAAEGSGEQD FTFETSGENT AVVAVEPDRR NQSPVDQGAT 250        260        270        280        290        300
GASQGLLDRK EVLGGVIAGG LVGLIFAVCL VGFMLYRMKK KDEGSYSLEE PKQANGGAYQ

310
KPTKQEEFYA
```

Most preferably, a TROY assay detects one or more soluble forms of TROY. TROY is a single-pass type I membrane protein having a large extracellular domain, most or all of which is present in soluble forms of TROY generated either through an alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in TROY:

| Residues | Length | Domain ID |
|---|---|---|
| 1-29 | 29 | signal sequence |
| 30-423 | 394 | TROY |
| 30-170 | 141 | extracellular |
| 171-191 | 21 | transmembrane |
| 192-423 | 232 | cytoplasmic |
| 416-423 | 8 | Replaced with EA in isoform 2 |

As used herein, the term "PIGR" or "Polymeric immunoglobulin receptor") refers to one or more polypeptides present in a biological sample that are derived from the PIGR precursor (Swiss-Prot P01833 (SEQ ID NO: 9)).

```
        10         20         30         40         50         60
MLLFVLTCLL AVFPAISTKS PIFGPEEVNS VEGNSVSITC YYPPTSVNRH TRKYWCRQGA 70         80         90        100        110        120
RGGCITLISS EGYVSSKYAG RANLTNFPEN GTFVVNIAQL SQDDSGRYKC GLGINSRGLS 130        140        150        160        170        180
FDVSLEVSQG PGLLNDTKVY TVDLGRTVTI NCPFKTENAQ KRKSLYKQIG LYPVLVIDSS 190        200        210        220        230        240
GYVNPNYTGR IRLDIQGTGQ LLFSVVINQL RLSDAGQYLC QAGDDSNSNK KNADLQVLKP 250        260        270        280        290        300
EPELVYEDLR GSVTFHCALG PEVANVAKFL CRQSSGENCD VVVNTLGKRA PAFEGRILLN 310        320        330        340        350        360
PQDKDGSFSV VITGLRKEDA GRYLCGAHSD GQLQEGSPIQ AWQLFVNEES TIPRSPTVVK 370        380        390        400        410        420
GVAGGSVAVL CPYNRKESKS IKYWCLWEGA QNGRCPLLVD SEGWVKAQYE GRLSLLEEPG 430        440        450        460        470        480
NGTFTVILNQ LTSRDAGFYW CLTNGDTLWR TTVEIKIIEG EPNLKVPGNV TAVLGETLKV 490        500        510        520        530        540
PCHFPCKFSS YEKYWCKWNN TGCQALPSQD EGPSKAFVNC DENSRLVSLT LNLVTRADEG 550        560        570        580        590        600
WYWCGVKQGH FYGETAAVYV AVEERKAAGS RDVSLAKADA APDEKVLDSG FREIENKAIQ 610        620        630        640        650        660
DPRLFAEEKA VADTRDQADG SRASVDSGSS EEQGGSSRAL VSTLVPLGLV LAVGAVAVGV 670        680        690        700        710        720
ARARHRKNVD RVSIRSYRTD ISMSDFENSR EFGANDNMGA SSITQETSLG GKEEFVATTE 730        740        750        760
STTETKEPKK AKRSSKEEAE MAYKDFLLQS STVAAEAQDG PQEA
```

Most preferably, a PIGR assay detects one or more soluble forms of PIGR. PIGR is a single-pass type I membrane protein having a large extracellular domain, most or all of which is present in soluble forms of PIGR generated either through an alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in PIGR:

| Residues | Length | Domain ID |
|---|---|---|
| 1-18 | 18 | signal sequence |
| 19-764 | 746 | PIGR |
| 19-638 | 620 | extracellular |
| 639-661 | 23 | transmembrane |
| 662-764 | 103 | cytoplasmic |
| 19-603 | 585 | Secretory component (a soluble form) |

As used herein, the terms "WAP four-disulfide core domain protein 2" "WAP4C" and "HE4" refer to one or more polypeptides present in a biological sample that are derived from a WAP four-disulfide core domain protein 2 precursor. The human precursor (Swiss-Prot entry Q14508) has the following sequence (SEQ ID NO: 1):

```
         10         20         30         40         50         60
MPACRLGPLA AALLLSLLLF GFTLVSGTGA EKTGVCPELQ ADQNCTQECV SDSECADNLK 70         80         90        100        110        120
CCSAGCATFC SLPNDKEGSC PQVNINFPQL GLCRDQCQVD SQCPGQMKCC RNGCGKVSCV
```

The following domains have been identified in WAP four-disulfide core domain protein 2:

| Residues | Length | Domain ID |
|---|---|---|
| 1-30 | 30 | signal sequence |
| 31-124 | 94 | WAP four-disulfide core domain protein 2 |

And the following alternative forms derived from the WAP four-disulfide core domain protein 2 precursor have been described:

| Residues | Length | Domain ID |
|---|---|---|
| 2-23 | 22 | → LQVQVNLPVSPLPTYPYSFF YP (SEQ ID NO: 2) in isoform 2. |
| 24-74 | 51 | Missing in isoform 2. |
| 27-74 | 48 | Missing in isoform 3. |
| 71-79 | 9 | → LLCPNGQLAE (SEQ ID NO: 3) in isoform 4. |
| 75-102 | 28 | → ALFHWHLKTRRLWEISGPRP RRPTWDSS (SEQ ID NO: 4) in isoform 5. |
| 80-124 | 45 | Missing in isoform 4. |
| 103-124 | 22 | Missing in isoform 5. |

Because production of marker fragments is an ongoing process that may be a function of, inter alia, the elapsed time between onset of an event triggering marker release into the tissues and the time the sample is obtained or analyzed; the elapsed time between sample acquisition and the time the sample is analyzed; the type of tissue sample at issue; the storage conditions; the quantity of proteolytic enzymes present; etc., it may be necessary to consider this degradation when both designing an assay for one or more markers, and when performing such an assay, in order to provide an accurate prognostic or diagnostic result. In addition, individual antibodies that distinguish amongst a plurality of marker fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample.

The failure to consider the degradation fragments that may be present in a clinical sample may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. Overestimation of the biologically active form(s) present in a sample may also have serious consequences for patient management. Considering the BNP example again, the BNP concentration may be used to determine if therapy is effective (e.g., by monitoring BNP to see if an elevated level is returning to normal upon treatment). The same "false positive" BNP result discussed above may lead the physician to continue, increase, or modify treatment because of the false impression that current therapy is ineffective.

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the cardiac injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

Preferred assays are "configured to detect" a particular marker. That an assay is "configured to detect" a marker means that an assay can generate a detectable signal indicative of the presence or amount of a physiologically relevant concentration of a particular marker of interest. Such an assay may, but need not, specifically detect a particular marker (i.e., detect a marker but not some or all related markers). Because an antibody epitope is on the order of 8 amino acids, an immunoassay will detect other polypeptides (e.g., related markers) so long as the other polypeptides contain the epitope(s) necessary to bind to the antibody used in the assay. Such other polypeptides are referred to as being "immunologically detectable" in the assay, and would include various isoforms (e.g., splice variants). In the case of a sandwich immunoassay, related markers must contain at least the two epitopes bound by the antibody used in the assay in order to be detected. Preferred immunologically detectable fragments comprise at least 8 contiguous residues of the marker or its biosynthetic parent.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

As used herein, a "plurality" refers to at least two. Preferably, a plurality refers to at least 3, more preferably at least 5, even more preferably at least 10, even more preferably at least 15, and most preferably at least 20. In particularly preferred embodiments, a plurality is a large number, i.e., at least about 100.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are "patients," i.e., living humans that are receiving medical care for a disease or condition. This includes persons with no defined illness who are being investigated for signs of pathology.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, amount, or change in amount of which is indicative of the presence, severity, or absence of the condition. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing morbidity or mortality in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient.

The term "correlating" or "relating" as used herein in reference to the use of markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels are correlated to a global probability or a particular outcome using ROC curves.

In certain embodiments, the methods described herein comprise the comparison of an assay result to a corresponding baseline result. The term "baseline result" as used herein refers to an assay value that is used as a comparison value (that is, to which a test result is compared). In practical terms, this means that a marker is measured in a sample from a subject, and the result is compared to the baseline result. A value above the baseline indicates a first likelihood of a diagnosis or prognosis, and a value below the baseline indicates a second likelihood of a diagnosis or prognosis.

A baseline can be selected in a number of manners well known to those of skill in the art. For example, data for a marker or markers (e.g., concentration in a body fluid, such as urine, blood, serum, or plasma) may be obtained from a population of subjects. The population of subjects is divided into at least two subpopulations. The first subpopulation includes those subjects who have been confirmed as having a disease, outcome, or, more generally, being in a first condition state. For example, this first subpopulation of patients may be those diagnosed with heart failure, and that suffered from a worsening of renal function. For convenience, subjects in this first subpopulation will be referred to as "diseased," although in fact, this subpopulation is actually selected for the presence of a particular characteristic of interest. The second subpopulation of subjects is formed from the subjects that do not fall within the first subpopulation. Subjects in this second set will hereinafter be referred to as "non-diseased."

A baseline result may then be selected to distinguish between the diseased and non-diseased subpopulation with an acceptable specificity and sensitivity. Changing the baseline merely trades off between the number of false positives and the number of false negatives resulting from the use of the particular marker under study. The effectiveness of a test having such an overlap is often expressed using a ROC (Receiver Operating Characteristic) curve. ROC curves are well known to those skilled in the art. The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In an alternative, an individual subject may provide their own baseline, in that a temporal change is used to indicate a particular diagnosis or prognosis. For example, one or more markers may be determined at an initial time to provide one or more baseline results, and then again at a later time, and the change (or lack thereof) in the marker level(s) over time determined In such embodiments, an increase in the marker from the initial time to the second time may be indicative of a particular prognosis, of a particular diagnosis, etc. Likewise, a decrease in the marker from the initial time to the second time may be indicative of a particular prognosis, of a particular diagnosis, etc. In such an embodiment, a plurality of markers need not change in concert with one another. Temporal changes in one or more markers may also be used together with single time point marker levels compared to a population-based baseline.

In certain embodiments, a baseline marker level is established for a subject, and a subsequent assay result for the same marker is determined. That subsequent result is compared to the baseline result, and a value above the baseline indicates worsening cardiac function, relative to a value below the baseline. Similarly, a value below the baseline indicates improved cardiac function, relative to a value above the baseline.

In certain embodiments, a baseline marker level is established for a subject, and a subsequent assay result for the same marker is determined. That subsequent result is compared to the baseline result, and a value above the baseline indicates an increased mortality risk, relative to a value below the baseline. Similarly, a value below the baseline indicates a decreased mortality risk, relative to a value above the baseline.

As discussed herein, the measurement of the level of a single marker may be augmented by additional markers. For example, other markers related to blood pressure regulation, including other natriuretic peptides and/or their related markers may be used together with, or separately from, BNP and/or its related markers. Suitable assays include, but are not limited to, assays that detect ANP, proANP, NT-proANP, CNP, Kininogen, CGRP II, urotensin II, BNP, NT-proBNP, proBNP, calcitonin gene related peptide, arg-Vasopressin, Endothelin-1 (and/or Big ET-1), Endothelin-2 (and/or Big ET-2), Endothelin-3 (and/or Big ET-3), procalcitonin, calcyphosine, adrenomedullin, aldosterone, angiotensin 1 (and/or angiotensinogen 1), angiotensin 2 (and/or angiotensinogen 2), angiotensin 3 (and/or angiotensinogen 3), Bradykinin, Tachykinin-3, calcitonin, Renin, Urodilatin, and Ghrelin, and/or one or more markers related thereto.

Various clinical variables may also be utilized as variables in the methods described herein. Examples of such variables include urine output levels, age, the presence or absence of one or more cardiovascular risk factors such as diabetes, hypertension, smoking status, etc. This list is not meant to be limiting.

Suitable methods for combining markers into a single composite value that may be used as if it is a single marker are described in detail in U.S. Provisional Patent Application No. 60/436,392 filed Dec. 24, 2002, PCT application US03/41426 filed Dec. 23, 2003, U.S. patent application Ser. No. 10/331,127 filed Dec. 27, 2002, and PCT application No. US03/41453, each of which is hereby incorporated by reference in its entirety, including all tables, figures, and claims. In an alternative, assay results may be used in an "n-of-m" type of approach. Using a two marker example of such methods, when either marker above its corresponding baseline value may signal a heart failure diagnosis or an increased risk of an adverse outcome (in n-of-m terms, this is a "1-of-2" result). If both are above the corresponding baselines (a "2-of-2" result), an even greater confidence in the subject's status may be indicated.

The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a "disease" will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., *Radiology* 143: 29-36 (1982).

Measures of test accuracy may also be obtained as described in Fischer et al., *Intensive Care Med.* 29: 1043-51, 2003, and used to determine the effectiveness of a given marker or panel of markers. These measures include sensitivity and specificity, predictive values, likelihood ratios, diagnostic odds ratios, and ROC curve areas. As discussed above, preferred tests and assays exhibit one or more of the following results on these various measures.

Preferably, a baseline is chosen to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman Access, Abbott AxSym, Roche ElecSys, Dade Behring Stratus systems are among the immunoassay analyzers that are capable of performing the immunoassays taught herein.

Preferably the markers are analyzed using an immunoassay, and most preferably sandwich immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Biological assays such as immunoassays require methods for detection, and one of the most common methods for quantitation of results is to conjugate an enzyme, fluorophore or other molecule to form an antibody-label conjugate. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.). Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of *Immunoassay*, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001. The antibodies could be immobilized onto a variety of solid supports, such as magnetic or chromatographic matrix particles, the surface of an assay plate (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot. When multiple assays are being performed, a plurality of separately addressable locations, each corresponding to a different marker and comprising antibodies that bind the appropriate marker, can be provided on a single solid support. The term "discrete" as used herein refers to areas of a surface that are non-contiguous. That is, two areas are discrete from one another if a border that is not part of either area completely surrounds each of the two areas. The term "independently addressable" as used herein refers to discrete areas of a surface from which a specific signal may be obtained.

For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses perform simultaneous assays of a plurality of markers using a single test device. Particularly useful physical formats comprise surfaces having a plurality of discrete, adressable locations for the detection of a plurality of different analytes. Such formats include protein microarrays, or "protein chips" (see, e.g., Ng and Ilag, J. Cell Mol. Med. 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

Preferred assay devices of the present invention will comprise, for one or more assays, a first antibody conjugated to a solid phase and a second antibody conjugated to a signal development element. Such assay devices are configured to perform a sandwich immunoassay for one or more analytes. These assay devices will preferably further comprise a sample application zone, and a flow path from the sample application zone to a second device region comprising the first antibody conjugated to a solid phase.

Flow of a sample in an assay device along the flow path may be driven passively (e.g., by capillary, hydrostatic, or other forces that do not require further manipulation of the device once sample is applied), actively (e.g., by application of force generated via mechanical pumps, electroosmotic pumps, centrifugal force, increased air pressure, etc.), or by a combination of active and passive driving forces. Most preferably, sample applied to the sample application zone will contact both a first antibody conjugated to a solid phase and a second antibody conjugated to a signal development element along the flow path (sandwich assay format). Additional elements, such as filters to separate plasma or serum from blood, mixing chambers, etc., may be included as required by the artisan. Exemplary devices are described in Chapter 41, entitled "Near Patient Tests: Triage® Cardiac System," in The *Immunoassay Handbook*, 2$^{nd}$ ed., David Wild, ed., Nature Publishing Group, 2001, which is hereby incorporated by reference in its entirety.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In another embodiment, the present invention provides a kit for the analysis of markers. Such a kit preferably comprises devises and reagents for the analysis of at least one test sample and instructions for performing the assay(s) of interest. Optionally the kits may contain one or more means for using information obtained from immunoassays performed for a marker panel to rule in or out certain diagnoses or prognoses. Other measurement strategies applicable to the methods described herein include chromatography (e.g., HPLC), mass spectrometry, receptor-based assays, and combinations of the foregoing.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Preferably, an antibody is selected that specifically binds a marker of interest. The term "specifically binds" is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ M$^{-1}$. Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c = K(n-r)$:

where r=moles of bound ligand/mole of receptor at equilibrium;

c=free ligand concentration at equilibrium;
K=equilibrium association constant; and
n=number of ligand binding sites per receptor molecule
By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1\times10^{-6}$ moles/liter, is more preferably at least about $1\times10^{-7}$ moles/liter, is even more preferably at least about $1\times10^{-8}$ moles/liter, is yet even more preferably at least about $1\times10^{-9}$ moles/liter, and is most preferably at least about $1\times10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The generation and selection of antibodies may be accomplished several ways. For example, one way is to purify polypeptides of interest or to synthesize the polypeptides of interest using, e.g., solid phase peptide synthesis methods well known in the art. See, e.g., Guide to Protein Purification, Murray P. Deutcher, ed., Meth. Enzymol. Vol 182 (1990); Solid Phase Peptide Synthesis, Greg B. Fields ed., Meth. Enzymol. Vol 289 (1997); Kiso et al., Chem. Pharm. Bull. (Tokyo) 38: 1192-99, 1990; Mostafavi et al., Biomed. Pept. Proteins Nucleic Acids 1: 255-60, 1995; Fujiwara et al., Chem. Pharm. Bull. (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target binds to the target and these phage are enriched by affinity screening to the target. The identity of polypeptides displayed from these enriched phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by phage display methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Alkaline phosphatase substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken for producing antibodies or binding fragments and screening and selecting for affinity and specificity for the various polypeptides, but these approaches do not change the scope of the invention.

EXAMPLES

The following examples serve to illustrate the present invention. These examples are in no way intended to limit the scope of the invention.

Example 1

Biochemical Analyses

Markers were measured using standard immunoassay techniques. These techniques involve the use of antibodies to specifically bind the analyte(s) of interest.

Immunoassays were performed using TECAN Genesis RSP 200/8 or Perkin Elmer Minitrak Workstations, using microtiter-based assays, or using microfluidic devices manufactured at Biosite Incorporated essentially as described in WO98/43739, WO98/08606, WO98/21563, and WO93/24231. Analytes may be measured using a sandwich immunoassay or using a competitive immunoassay as appropriate, depending on the characteristics and concentration range of the analyte of interest.

In certain cases, multiplexed and single-assay, bead-based immunoassays were performed on human plasma (or serum) samples in microtiter plates. The primary antibody for each assay was conjugated to modified paramagnetic Luminex® beads obtained from Radix Biosolutions. Either the secondary antibodies (sandwich assays) or the antigens (competitive assays) were biotinylated. Fluorescent signals were generated using Streptavidin-R-Phycoerythrin (SA-RPE: Prozyme PJ31S). All assays were heterogeneous and required multiple washes; washes were performed in 96-well plates placed on a 96-well magnetic ring stand (Ambion) in order to keep the paramagnetic beads from being removed. All liquid handling steps were performed with a Beckman Biomek FX.

In other cases, a monoclonal antibody directed against a selected analyte was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed by washing. The solution containing any unbound antibody was removed, and the wells washed with a wash buffer, consisting of 20 mM borate (pH 7.42) containing 150 mM NaCl, 0.1% sodium azide, and 0.02% Tween-20. This formed the "anti-marker" in the microtiter plate. Another monoclonal antibody directed against the same analyte was conjugated to alkaline phosphatase, for example using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.). The plasma samples (10 µL) containing added HAMA inhibitors were pipetted into the microtiter plate wells, and incubated for 60 min. The sample was then removed and the wells washed with a wash buffer. The antibody-alkaline phosphatase conjugate was then added to the wells and incubated for an additional 60 min, after which time, the antibody conjugate was removed and the wells washed with a wash buffer. A substrate, (AttoPhos®, Promega, Madison, Wis.) was added to the wells, and the rate of formation of the fluorescent product is related to the concentration of the analyte in the sample tested.

An 8-point calibration curve was made gravimetrically by spiking each antigen into the calibration matrix. For sandwich assays, this matrix was plasma (or serum) from healthy donors; one of the eight points included free antibody to neutralize any endogenous antigen that was present. For competitive assays, this matrix was CD8 buffer (10 mmol/L Tris-HCl (pH 8.0), 150 mmol/L NaCl, 1 mmol/L MgCl2, 0.1 mmol/L ZnCl2, 10 mL/L polyvinyl alcohol (MW 9000-10 000), 10 g/L bovine serum albumin, and 1 g/L NaN3). Samples were stored in 384-well microtiter plates keep at −70° C. A source plate was made by thawing the sample plate at 37° C., and then adding replicates of the 8-point calibration curve.

The assays were performed at room temperature. The bead-based primary antibody solution was added to a 384-well assay plate (10ul/well) and then samples were added from the source plate (10ul/well), mixed, and incubated one hour. Note, competitive assays were run in different assay plates than the sandwich assays, and the biotinylated antigen was added to the samples before transfer to the assay plate. Each 384-well plate was split into four 96-well plates for subsequent processing. The plates were washed as described above; the sandwich assays were incubated with biotinylated secondary antibodies and washed again. The assay mixtures were labeled with SA-RPE, washed, and read using a Luminex® LX200 reader; the median signal for each assay for was used for data reduction of each sample. The antigen concentrations were calculated using a standard curve determined by fitting a five parameter logistic function to the signals obtained for the 8-point calibration curves.

The assays were calibrated using purified proteins (that is either the same as or related to the selected analyte, and that can be detected in the assay) diluted gravimetrically into EDTA plasma treated in the same manner as the sample population specimens. Endogenous levels of the analyte present in the plasma prior to addition of the purified marker protein was measured and taken into account in assigning the marker values in the calibrators. When necessary to reduce endogenous levels in the calibrators, the endogenous analyte was stripped from the plasma using standard immunoaffinity methods. Calibrators were assayed in the same manner as the sample population specimens, and the resulting data used to construct a "dose-response" curve (assay signal as a function of analyte concentration), which may be used to determine analyte concentrations from assay signals obtained from subject specimens.

In the case of assays performed using microfluidic devices, devices used to perform assays were essentially as described in Chapter 41, entitled "Near Patient Tests: Triage® Cardiac System," in *The Immunoassay Handbook*, $2^{nd}$ ed., David Wild, ed., Nature Publishing Group, 2001.

For sandwich immunoassays, a plasma sample was added to the microfluidic device that contains all the necessary assay reagents, including HAMA inhibitors, in dried form. The plasma passed through a filter to remove particulate matter. Plasma entered a "reaction chamber" by capillary action. This reaction chamber contained fluorescent latex particle-antibody conjugates (hereafter called FETL-antibody conjugates) appropriate to an analyte of interest, and may contain FETL-antibody conjugates to several selected analytes. The FETL-antibody conjugates dissolved into the plasma to form a reaction mixture, which was held in the reaction chamber for an incubation period (about a minute) to allow the analyte(s) of interest in the plasma to bind to the antibodies. After the incubation period, the reaction mixture moved down the detection lane by capillary action. Antibodies to the analyte(s) of interest were immobilized in discrete capture zones on the surface of a "detection lane." Analyte/antibody-FETL complexes formed in the reaction chamber were captured on an appropriate detection zone to form a sandwich complex, while unbound FETL-antibody conjugates were washed from the detection lane into a waste chamber by excess plasma. The amount of analyte/antibody-FETL complex bound on a capture zone was quantified with a fluorometer (Triage® MeterPlus, Biosite Incorporated) and was related to the amount of the selected analyte in the plasma specimen.

Individual assays were configured to bind the following markers: WAP4C, BNP, ESAM, LTBR, Mesothelin, Syndecan-1, TROY, and PIGR. Reported units are as follows: WAP4C, ng/mL; BNP pg/mL; ESAM ng/mL; LTBR ng/mL; Mesothelin ng/mL; PIGR ng/mL; Syndecan-1 ng/mL; Troy ng/mL. Descriptive statistics are presented in the following table. "N" is the number of subjects in each group; "$25^{th}$", "$50^{th}$", and "$75^{th}$" refer to the value at the $25^{th}$, $50^{th}$, and $75^{th}$ percentile, respectively; "SD" is the standard deviation; SE of Mean is the standard error for the mean value.

Example 2

Descriptive Statistics for Assays

TABLE 1

| Marker | Group | N | Min | Mean | SE of Mean | Max | 25th | 50th | 75th | SD |
|---|---|---|---|---|---|---|---|---|---|---|
| BNP | Clinical Normal | 112 | 18.0 | 52.0 | 8.1 | 847.2 | 18.0 | 28.8 | 48.6 | 85.9 |
| BNP | ACC/AHA Stage A/B Asymptomatic Heart Failure | 25 | 18.0 | 88.4 | 22.0 | 424.4 | 20.1 | 31.2 | 132.3 | 109.8 |

TABLE 1-continued

| Marker | Group | N | Min | Mean | SE of Mean | Max | 25th | 50th | 75th | SD |
|---|---|---|---|---|---|---|---|---|---|---|
| BNP | Symptomatic Heart Failure, NYHA I-II | 35 | 18.0 | 367.2 | 97.8 | 2900.0 | 45.4 | 184.4 | 349.8 | 578.7 |
| BNP | BNP <=100 pg/mL Clinical Normal | 98 | 18.0 | 32.2 | 1.9 | 98.8 | 18.0 | 23.4 | 42.6 | 18.4 |
| BNP | BNP <=100 pg/mL ACC/AHA Stage A/B Asymptomatic Heart Failure | 18 | 18.0 | 29.9 | 3.5 | 75.3 | 18.0 | 27.2 | 35.4 | 14.8 |
| BNP | BNP <=100 pg/mL Symptomatic Heart Failure, NYHA I-II | 13 | 18.0 | 41.5 | 6.9 | 83.9 | 20.4 | 41.3 | 59.9 | 24.7 |
| ESAM | Clinical Normal | 112 | 5.8 | 22.7 | 0.6 | 41.6 | 19.0 | 21.9 | 25.5 | 6.4 |
| ESAM | ACC/AHA Stage A/B Asymptomatic Heart Failure | 25 | 28.2 | 42.7 | 2.4 | 75.5 | 34.3 | 42.1 | 45.6 | 11.9 |
| ESAM | Symptomatic Heart Failure, NYHA I-II | 35 | 28.6 | 56.0 | 2.9 | 84.3 | 42.5 | 57.2 | 68.4 | 17.4 |
| ESAM | BNP <=100 pg/mL Clinical Normal | 98 | 5.8 | 22.0 | 0.6 | 41.4 | 18.7 | 21.8 | 24.2 | 6.0 |
| ESAM | BNP <=100 pg/mL ACC/AHA Stage A/B Asymptomatic Heart Failure | 18 | 28.2 | 39.2 | 1.8 | 57.8 | 34.3 | 39.7 | 43.9 | 7.5 |
| ESAM | BNP <=100 pg/mL Symptomatic Heart Failure, NYHA I-II | 13 | 31.7 | 57.6 | 5.3 | 82.0 | 39.2 | 57.5 | 76.7 | 19.0 |
| LTBR | Clinical Normal | 112 | 0.4 | 0.5 | 0.0 | 1.0 | 0.4 | 0.4 | 0.4 | 0.1 |
| LTBR | ACC/AHA Stage A/B Asymptomatic Heart Failure | 25 | 0.4 | 1.1 | 0.1 | 2.7 | 0.7 | 0.9 | 1.4 | 0.5 |
| LTBR | Symptomatic Heart Failure, NYHA I-II | 35 | 0.5 | 2.0 | 0.2 | 5.4 | 1.0 | 1.8 | 2.8 | 1.2 |
| LTBR | BNP <=100 pg/mL Clinical Normal | 98 | 0.4 | 0.5 | 0.0 | 1.0 | 0.4 | 0.4 | 0.4 | 0.1 |
| LTBR | BNP <=100 pg/mL ACC/AHA Stage A/B Asymptomatic Heart Failure | 18 | 0.4 | 1.0 | 0.1 | 1.8 | 0.6 | 0.8 | 1.3 | 0.4 |
| LTBR | BNP <=100 pg/mL Symptomatic Heart Failure, NYHA I-II | 13 | 0.6 | 2.0 | 0.3 | 4.4 | 1.0 | 1.6 | 3.2 | 1.2 |
| Mesothelin | Clinical Normal | 112 | 0.4 | 5.1 | 0.3 | 22.9 | 2.5 | 4.3 | 6.6 | 3.6 |
| Mesothelin | ACC/AHA Stage A/B Asymptomatic Heart Failure | 25 | 1.0 | 27.4 | 4.1 | 87.0 | 12.0 | 20.3 | 38.1 | 20.3 |
| Mesothelin | Symptomatic Heart Failure, NYHA I-II | 35 | 1.7 | 45.7 | 6.0 | 147.6 | 19.5 | 43.8 | 59.0 | 35.4 |

TABLE 1-continued

| Marker | Group | N | Min | Mean | SE of Mean | Max | 25th | 50th | 75th | SD |
|---|---|---|---|---|---|---|---|---|---|---|
| Mesothelin | BNP <=100 pg/mL Clinical Normal | 98 | 0.4 | 4.7 | 0.3 | 14.6 | 2.4 | 4.0 | 6.3 | 3.0 |
| Mesothelin | BNP <=100 pg/mL ACC/AHA Stage A/B Asymptomatic Heart Failure | 18 | 8.5 | 28.3 | 5.0 | 87.0 | 12.4 | 18.9 | 43.8 | 21.2 |
| Mesothelin | BNP <=100 pg/mL Symptomatic Heart Failure, NYHA I-II | 13 | 4.4 | 45.2 | 10.4 | 147.6 | 18.7 | 46.0 | 59.7 | 37.6 |
| PIGR | Clinical Normal | 112 | 10.2 | 58.6 | 2.9 | 169.6 | 40.5 | 52.3 | 68.9 | 30.6 |
| PIGR | ACC/AHA Stage A/B Asymptomatic Heart Failure | 25 | 11.1 | 209.8 | 41.4 | 829.4 | 49.7 | 177.2 | 279.6 | 206.8 |
| PIGR | Symptomatic Heart Failure, NYHA I-II | 35 | 13.1 | 299.8 | 34.1 | 778.5 | 135.3 | 289.5 | 453.2 | 201.7 |
| PIGR | BNP <=100 pg/mL Clinical Normal | 98 | 10.2 | 53.8 | 2.5 | 161.1 | 39.2 | 49.6 | 64.4 | 24.4 |
| PIGR | BNP <=100 pg/mL ACC/AHA Stage A/B Asymptomatic Heart Failure | 18 | 11.1 | 147.3 | 27.6 | 396.5 | 37.0 | 128.4 | 217.3 | 117.3 |
| PIGR | BNP <=100 pg/mL Symptomatic Heart Failure, NYHA I-II | 13 | 13.1 | 133.2 | 28.7 | 296.5 | 58.3 | 94.7 | 208.7 | 103.4 |
| Syndecan-1 | Clinical Normal | 112 | 0.8 | 2.9 | 0.1 | 11.7 | 2.1 | 2.7 | 3.4 | 1.4 |
| Syndecan-1 | ACC/AHA Stage A/B Asymptomatic Heart Failure | 25 | 5.8 | 11.1 | 1.0 | 25.6 | 7.8 | 8.7 | 12.9 | 5.2 |
| Syndecan-1 | Symptomatic Heart Failure, NYHA I-II | 35 | 3.7 | 15.0 | 1.4 | 36.4 | 10.8 | 14.5 | 15.9 | 8.1 |
| Syndecan-1 | BNP <=100 pg/mL Clinical Normal | 98 | 0.8 | 2.8 | 0.1 | 11.7 | 1.9 | 2.6 | 3.3 | 1.4 |
| Syndecan-1 | BNP <=100 pg/mL ACC/AHA Stage A/B Asymptomatic Heart Failure | 18 | 6.3 | 11.4 | 1.3 | 25.6 | 8.4 | 8.7 | 12.3 | 5.6 |
| Syndecan-1 | BNP <=100 pg/mL Symptomatic Heart Failure, NYHA I-II | 13 | 3.7 | 15.5 | 2.5 | 36.4 | 11.0 | 14.8 | 16.0 | 9.1 |
| Troy | Clinical Normal | 112 | 0.2 | 0.5 | 0.0 | 1.4 | 0.4 | 0.5 | 0.6 | 0.2 |
| Troy | ACC/AHA Stage A/B Asymptomatic Heart Failure | 25 | 0.4 | 1.1 | 0.1 | 3.4 | 0.7 | 0.9 | 1.2 | 0.6 |
| Troy | Symptomatic Heart Failure, NYHA I-II | 35 | 0.5 | 1.6 | 0.1 | 3.7 | 1.1 | 1.4 | 1.8 | 0.8 |
| Troy | BNP <=100 pg/mL Clinical Normal | 98 | 0.2 | 0.5 | 0.0 | 1.4 | 0.4 | 0.5 | 0.6 | 0.2 |

TABLE 1-continued

| Marker | Group | N | Min | Mean | SE of Mean | Max | 25th | 50th | 75th | SD |
|---|---|---|---|---|---|---|---|---|---|---|
| Troy | BNP <=100 pg/mL ACC/AHA Stage A/B Asymptomatic Heart Failure | 18 | 0.4 | 1.0 | 0.1 | 2.2 | 0.7 | 0.9 | 1.1 | 0.4 |
| Troy | BNP <=100 pg/mL Symptomatic Heart Failure, NYHA I-II | 13 | 0.6 | 1.4 | 0.2 | 2.9 | 0.9 | 1.4 | 1.8 | 0.7 |

TABLE 2

| Marker | Group | N | Min | Max | Median | Mean | SE of mean |
|---|---|---|---|---|---|---|---|
| BNP | CVD Death Yes | 275 | 30.0 | 2600.0 | 69.2 | 132.0 | 13.0 |
| BNP | CVD Death No | 1464 | 30.0 | 2600.0 | 30.0 | 73.6 | 3.3 |
| BNP | All | 1739 | 30.0 | 2600.0 | 35.5 | 82.8 | 3.5 |
| ESAM | CVD Death Yes | 275 | 9.1 | 71.2 | 31.0 | 31.9 | 0.5 |
| ESAM | CVD Death No | 1464 | 0.2 | 75.8 | 28.1 | 28.9 | 0.2 |
| ESAM | All | 1739 | 0.2 | 75.8 | 28.5 | 29.4 | 0.2 |
| LTBR | CVD Death Yes | 275 | 0.3 | 4.9 | 0.3 | 0.5 | 0.0 |
| LTBR | CVD Death No | 1464 | 0.3 | 18.2 | 0.3 | 0.5 | 0.0 |
| LTBR | All | 1739 | 0.3 | 18.2 | 0.3 | 0.5 | 0.0 |
| Mesothelin | CVD Death Yes | 275 | 0.5 | 275.5 | 9.6 | 13.2 | 1.1 |
| Mesothelin | CVD Death No | 1464 | 0.1 | 380.0 | 7.7 | 11.4 | 0.5 |
| Mesothelin | All | 1739 | 0.1 | 380.0 | 8.0 | 11.7 | 0.4 |
| PIGR | CVD Death Yes | 275 | 14.5 | 605.4 | 110.1 | 128.1 | 4.7 |
| PIGR | CVD Death No | 1466 | 4.8 | 715.7 | 81.0 | 94.4 | 1.6 |
| PIGR | All | 1741 | 4.8 | 715.7 | 84.2 | 99.7 | 1.6 |
| Syndecan-1 | CVD Death Yes | 275 | 0.9 | 20.1 | 3.9 | 4.4 | 0.1 |
| Syndecan-1 | CVD Death No | 1465 | 0.2 | 35.2 | 3.8 | 4.6 | 0.1 |
| Syndecan-1 | All | 1740 | 0.2 | 35.2 | 3.8 | 4.6 | 0.1 |
| Troy | CVD Death Yes | 275 | 0.2 | 3.9 | 0.8 | 0.9 | 0.0 |
| Troy | CVD Death No | 1463 | 0.0 | 9.6 | 0.6 | 0.7 | 0.0 |
| Troy | All | 1738 | 0.0 | 9.6 | 0.6 | 0.7 | 0.0 |

Example 2

Use of Biomarkers to Diagnose Heart Failure

Two cohorts were defined as described in each of the following tables. The ability to distinguish Cohort 1 from Cohort 2 was determined using ROC analysis. The meaning and use of the area under a receiver operating characteristic (ROC) curve is described in Radiology (1982) 143: 29-36 (the contents of which are incorporated herein by reference). An AUC<0.5 is indicative of a negative going marker (meaning the marker falls in Cohort 2 as compared to Cohort 1) for the comparison, and an AUC>0.5 is indicative of a positive going marker (meaning the marker rises in Cohort 2 as compared to Cohort 1) for the comparison.

TABLE 3

| N, Cohort 1: Clinical Normal | N, Cohort 2: Symptomatic Heart Failure, NYHA I-II | Biomarker | ROC AUC | ROC AUC 95% CI | P-value: |
|---|---|---|---|---|---|
| 112 | 35 | BNP | 0.81 | 0.71-0.98 | <0.0001 |
| 112 | 35 | ESAM | 0.98 | 0.96-1.00 | <0.0001 |
| 112 | 35 | LTBR | 0.99 | 0.98-1.00 | <0.0001 |
| 112 | 35 | Mesothelin | 0.94 | 0.88-1.00 | <0.0001 |
| 112 | 35 | Syndecan-1 | 0.98 | 0.97-1.00 | <0.0001 |

TABLE 4

| N, Cohort 1: BNP <= 100 pg/mL Clinical Normal | N, Cohort 2: BNP <= 100 pg/mL Symptomatic Heart Failure, NYHA I/II | Biomarker | ROC AUC | ROC AUC 95% CI | P-value: |
|---|---|---|---|---|---|
| 98 | 13 | BNP | 0.59 | 0.397 - 0.785 | 0.1791 |
| 98 | 13 | ESAM | 0.99 | 0.97 - 1.00 | <0.0001 |
| 98 | 13 | LTBR | 0.99 | 0.98 - 1.00 | <0.0001 |
| 98 | 13 | Mesothelin | 0.95 | 0.88 - 1.00 | <0.0001 |
| 98 | 13 | Syndecan-1 | 0.98 | 0.94 - 1.00 | <0.0001 |

TABLE 5

| N, Cohort 1: Clinical Normal | N, Cohort 2: ACC/AHA Stage A/B Asymptomatic Heart Failure | Biomarker | ROC AUC | ROC AUC 95% CI | P-value: H0: Area ≤ 0.5. H1: Area > 0.5. |
|---|---|---|---|---|---|
| 112 | 25 | BNP | 0.54 | 0.39 - 0.69 | 0.2964 |
| 112 | 25 | ESAM | 0.97 | 0.94 - 0.99 | <0.0001 |
| 112 | 25 | LTBR | 0.89 | 0.78 - 1.00 | <0.0001 |
| 112 | 25 | Mesothelin | 0.93 | 0.85 - 1.00 | <0.0001 |
| 112 | 25 | Syndecan-1 | 0.99 | 0.98 - 1.00 | <0.0001 |

TABLE 6

| N, Cohort 1: BNP <= 100 pg/mL Clinical Normal | N, Cohort 2: BNP <= 100 pg/mL ACC/AHA Stage A/B Asymptomatic Heart Failure | Biomarker | ROC AUC | ROC AUC 95% CI | P-value: H0: Area ≤ 0.5. H1: Area >0.5. |
|---|---|---|---|---|---|
| 98 | 18 | BNP | 0.57 | 0.26 - 0.59 | 0.8088 |
| 98 | 18 | ESAM | 0.97 | 0.95 - 1.00 | <0.0001 |
| 98 | 18 | LTBR | 0.91 | 0.80 - 1.00 | <0.0001 |

TABLE 6-continued

| N, Cohort 1: BNP <= 100 pg/mL Clinical Normal | N, Cohort 2: BNP <= 100 pg/mL ACC/AHA Stage A/B Asymptomatic Heart Failure | Biomarker | ROC AUC | ROC AUC 95% CI | P-value: H0: Area ≤ 0.5. H1: Area >0.5. |
|---|---|---|---|---|---|
| 98 | 18 | Mesothelin | 0.98 | 0.96 - 1.00 | <0.0001 |
| 98 | 18 | Syndecan-1 | 0.99 | 0.98 - 1.00 | <0.0001 |

As can be seen by these results, each of BNP, ESAM, LTBR, Mesothelin, and Syndecan-1 is able to distinguish NYHA class 1 or 2 heart failure patients from clinically normal individuals (Table 1). It is notable that ESAM, LTBR, Mesothelin, and Syndecan-1 each demonstrate a superior ROC area to BNP, which is currently the best established heart failure marker in clinical use Importantly, each of ESAM, LTBR, Mesothelin, and Syndecan-1 are able to identify NYHA class 1 or 2 heart failure patients with a plasma BNP level≤100 pg/mL (a level often considered to be diagnostically negative for heart failure) with high confidence (Table 2).

Also, in those patients adjudged clinically as having ACC/AHA Stage A/B asymptomatic heart failure, BNP is an extremely poor diagnostic marker (Tables 3 and 4), with a ROC area that is not significantly better than random. In contrast, each of ESAM, LTBR, Mesothelin, and Syndecan-1 are able to identify such asymptomatic heart failure with high confidence.

Example 3

Use of Biomarkers Prognostically

We computed adjusted odds ratios (AOR) for CVD and CHD death by marker level quartile, normalized to first quartile odds. For the fourth quartile, the AOR can be expressed as in the following equation:

$$AOR(Q4) = \frac{\frac{P(+|Q4, X)}{P(-|Q4, X)}}{\frac{P(+|Q1, X)}{P(-|Q1, X)}}$$

In the equation, $P(+|Q4, X)$ is the probability of death, given that the subject's marker level fell within the fourth quartile, and that the value of the covariates to be adjusted for (e.g. age, gender) is X for all subjects used in the calculation. The numerator and denominator are the odds of death versus survival for the fourth and first quartiles respectively. We also used follow-up data on the clinical endpoints CVD and CHD death to compute empirical survival probabilities. We also modeled these data using Cox proportional hazards (CPH) regression [2], which allowed us to estimate the impact of marker level, age, gender, etc. on survival. Empirical estimates of the survival probability were computed using the Kaplan-Meier method, which accounts for censored data (i.e. subjects that exit the study due to causes other than the endpoint of interest). Appropriate methods which may be used for the analysis may be found in Dupont, William Dudley; Statistical modeling for biomedical researchers: a simple introduction to the analysis of complex data; Cambridge University Press; 2002; Collett, David; Modeling survival data in medical research; CRC Press; 2003; and Bender, Ralf, Augustin, Thomas and Blettner, Maria; Statistics in Medicine; 24; 1713; 2005. (The contents of which are incorporated herein by reference).

Risk of cardiovascular disease death; International Classification of Disease—9th Revision criteria. CVD death included deaths assigned codes 390 through 459:

TABLE 7

| Biomarker | Unadjusted exp (Beta) | Unadjusted P-Value | Unadjusted Hazard Ratio quartile 4 v. quartile 1 | BNP-adjusted exp (Beta) | BNP-adjusted P-Value | BNP-adjusted Hazard Ratio quartile 4 v. quartile 1 |
|---|---|---|---|---|---|---|
| Troy | 1.6 | 1.66E-10 | 4.1 | 1.5 | 4.41E-09 | 3.7 |
| PIGR | 1.7 | 2.68E-13 | 5.2 | 1.7 | 1.01E-11 | 4.7 |
| BNP | 1.6 | 5.35E-14 | 4.3 | N/A | N/A | N/A |

It is noted in these data that TROY and PIGR remain statistically significant predictors of mortality following adjustment of the model for BNP concentrations.

Example 4

Use of WAP4C Prognostically

The following study utilizes patents from the Coordinating Study Evaluating Outcomes of Advising and Counseling in Heart Failure (COACH) study, a multicenter, randomized, controlled trial in which 1023 patients were enrolled after hospitalization because of HF. See, Arch. Intern. Med. 168: 316-24, 2008. Patients were assigned to 1 of 3 groups: a control group (follow-up by a cardiologist) and 2 intervention groups with additional basic or intensive support by a nurse specializing in management of patients with HF. Patients were studied for 18 months. Primary end points were time to death or rehospitalization because of HF and the number of days lost to death or hospitalization.

A baseline WAP four-disulfide core domain protein 2 measurement was obtained from the COACH subjects. The baseline draw was taken after randomization to either the care or active intervention pathway as described above, which was to have occurred within 2 days of HF admission. Descriptive statistics obtained from this measurement are presented in the following table. "N" is the number of subjects in each group; "$25^{th}$", "$50^{th}$", and "$75^{th}$" refer to the value at the $25^{th}$, $50^{th}$, and $75^{th}$ percentile, respectively; "SD" is the standard deviation; SE of Mean is the standard error for the mean value.

TABLE 8

| | NO DEATH | NO HF rehosp | NO DEATH, NO HF rehosp | DEATH, all cause | HF rehosp | DEATH, all cause OR HF rehosp |
|---|---|---|---|---|---|---|
| N | 479 | 419 | 327 | 92 | 148 | 240 |
| 0th percentile | 0.71 | 0.71 | 0.71 | 2.22 | 1.03 | 1.03 |
| 25th percentile | 3.18 | 3.15 | 2.87 | 4.87 | 4.06 | 4.41 |
| 50th percentile | 5.17 | 5.17 | 4.67 | 7.66 | 7.94 | 7.81 |
| 75th percentile | 9.26 | 8.69 | 7.66 | 17.17 | 12.29 | 13.93 |
| 100th percentile | 42.72 | 63.26 | 33.94 | 63.26 | 30.19 | 63.26 |

TABLE 8-continued

|  | NO DEATH | NO HF rehosp | NO DEATH, NO HF rehosp | DEATH, all cause | HF rehosp | DEATH, all cause OR HF rehosp |
| --- | --- | --- | --- | --- | --- | --- |
| Mean | 7.112 | 7.47 | 6.06 | 12.50 | 9.10 | 10.41 |
| SE | 0.262 | 0.35 | 0.27 | 1.16 | 0.51 | 0.55 |
| Variance | 32.60 | 51.93 | 22.96 | 123.49 | 38.75 | 73.60 |
| SD | 5.71 | 7.21 | 4.79 | 11.11 | 6.22 | 8.58 |

The ability of the baseline WAP four-disulfide core domain protein 2 measurement to identify outcome risk was determined We computed adjusted odds ratios (AOR) for CVD and CHD death by marker level quartile, normalized to first quartile odds. For the fourth quartile, the AOR can be expressed as in the following equation:

$$AOR(Q4) = \frac{\frac{P(+|Q4, X)}{P(-|Q4, X)}}{\frac{P(+|Q1, X)}{P(-|Q1, X)}}$$

In the equation, P(+|Q4, X) is the probability of death, given that the subject's marker level fell within the fourth quartile, and that the value of the covariates to be adjusted for (e.g. age, gender) is X for all subjects used in the calculation. The numerator and denominator are the odds of death versus survival for the fourth and first quartiles respectively. We also used follow-up data on the clinical endpoints CVD and CHD death to compute empirical survival probabilities. We also modeled these data using Cox proportional hazards (CPH) regression [2], which allowed us to estimate the impact of marker level, age, gender, etc. on survival. Empirical estimates of the survival probability were computed using the Kaplan-Meier method, which accounts for censored data (i.e. subjects that exit the study due to causes other than the endpoint of interest).

TABLE 9

Event: HF rehospitalization or death (all cause)

|  | Hazard ratio (3rd vs. 1st tertiles) | P-Value |
| --- | --- | --- |
| WAP4C | 3.30 | 1.8E-12 |
| WAP4C, adjusted for COACH treatment group, age, gender, NYHA class at enrollment | 2.80 | 4.0E-08 |
| WAP4C, adjusted for COACH treatment group, age, gender, NYHA class at enrollment, and BNP | 2.26 | 2.7E-05 |
| WAP4C, adjusted for COACH treatment group, age, gender, diabetes, LVEF, and NYHA class at enrollment | 2.65 | 1.6E-06 |
| WAP4C, adjusted for COACH treatment group, age, gender, diabetes, LVEF, NYHA class at enrollment, and BNP | 2.00 | 1.3E-03 |

TABLE 10

Event: HF rehospitalization

|  | Hazard ratio (3rd vs. 1st tertiles) | P-Value |
| --- | --- | --- |
| WAP4C | 2.83 | 3.3E-07 |
| WAP4C, adjusted for COACH treatment group, age, gender, NYHA class at enrollment | 2.70 | 1.3E-05 |
| WAP4C, adjusted for COACH treatment group, age, gender, NYHA class at enrollment, and BNP | 2.32 | 3.6E-04 |
| WAP4C, adjusted for COACH treatment group, age, gender, diabetes, LVEF, and NYHA class at enrollment | 2.79 | 2.3E-05 |
| WAP4C, adjusted for COACH treatment group, age, gender, diabetes, LVEF, NYHA class at enrollment, and BNP | 2.27 | 1.4E-03 |

TABLE 11

Event: HF rehospitalization or death (all cause)

|  | Odds Ratio (3rd v.1st tertile) | P-Value |
| --- | --- | --- |
| WAP4C | 4.21 | <0.001 |
| WAP4C, adjusted for COACH treatment group, age, and gender | 3.26 | <0.001 |
| WAP4C, adjusted for COACH treatment group, age, gender, NYHA class at enrollment, and BNP | 2.69 | <0.001 |

TABLE 12

Event: HF rehospitalization

|  | Odds Ratio (3rd v.1st tertile) | P-Value |
| --- | --- | --- |
| WAP4C | 2.47 | <0.001 |
| WAP4C, adjusted for COACH treatment group, age, and gender | 2.37 | 0.001 |
| WAP4C, adjusted for COACH treatment group, age, gender, NYHA class at enrollment, and BNP | 2.21 | 0.005 |

TABLE 13

| Clinical Dichotomy | AUC (confidence interval) | S.E. | p-Value | N (control) | N (disease) |
|---|---|---|---|---|---|
| HF rehospitalization or death (all cause) | 0.69 (0.64-0.73) | 0.023 | <0.001 | 327 | 240 |
| HF rehospitalization or death (all cause) (T > 180 days) | 0.61 (0.55-0.68) | 0.032 | <0.001 | 321 | 101 |
| HF rehospitalization or death (all cause) (T <= 180 days) | 0.72 (0.67-0.77) | 0.026 | <0.001 | 428 | 139 |
| HF rehospitalization | 0.61 (0.56-0.66) | 0.027 | <0.001 | 419 | 148 |
| HF rehospitalization (T > 180 days) | 0.60 (0.52-0.67) | 0.037 | 0.005 | 353 | 69 |
| HF rehospitalization (T <= 180 days) | 0.66 (0.59-0.72) | 0.034 | <0.001 | 488 | 79 |

The following study utilizes patents from the Heart and Soul study (Whooley et al., *J. Am. Med. Assoc.* 300: 2379-2388, 2008). The patient population consisted of outpatients with documented coronary artery disease identified from databases at two Department of Veterans Affairs Medical Centers (San Francisco VA Medical Center and the VA Palo Alto Health Care System, California), one university medical center (University of California, San Francisco), and nine public health clinics in the Community Health Network of San Francisco. Patients were eligible to participate if they had at least one of the following: a history of myocardial infarction, angiographic evidence of at least 50% stenosis in one or more coronary vessels, prior evidence of exercise-induced ischemia by treadmill or nuclear testing, a history of coronary revascularization, or a diagnosis of coronary artery disease documented by an internist or cardiologist. Between Sep. 11, 2000, and Dec. 20, 2002, a total of 1024 participants were enrolled: 240 from the public health clinics, 346 from the university medical center, and 438 from the VA medical centers.

Clinical endpoints of interest were cardiovascular death, cardiovascular Hospitalization, and heart failure. Plasma BNP, WAP4C, and the combined results of these two markers measured at enrollment were used to assess risk of an event over a 10 year follow-up period.

TABLE 14

Event: HF rehospitalization and/or all-cause death

| | Hazard ratio (3rd vs 1st tertile) | P-value |
|---|---|---|
| WAP4C | 4.9162 | 2.06E-25 |
| WAP4C, adjusted for age and gender | 3.9068 | 1.30E-16 |
| WAP4C, adjusted for age, gender, and BNP | 3.2658 | 3.75E-12 |
| WAP4C, adjusted for age, gender, diabetes, and LVEF | 3.4416 | 4.98E-14 |
| WAP4C, adjusted for age, gender, diabetes, LVEF, and BNP | 2.9954 | 1.08E-10 |

TABLE 15

Event: HF rehospitalization

| | Hazard ratio (3rd vs 1st tertile) | P-value |
|---|---|---|
| WAP4C | 6.8519 | 7.57E-14 |
| WAP4C, adjusted for age and gender | 5.4647 | 4.95E-10 |
| WAP4C, adjusted for age, gender, and BNP | 3.8442 | 2.25E-06 |
| WAP4C, adjusted for age, gender, diabetes, and LVEF | 4.3588 | 4.88E-08 |
| WAP4C, adjusted for age, gender, diabetes, LVEF, and BNP | 3.2062 | 4.04E-05 |

TABLE 16

Event: HF rehospitalization and/or all-cause death

| | Odds ratio (3rd vs 1st tertile) | P-value |
|---|---|---|
| WAP4C | 7.6886 | 6.60E-28 |
| WAP4C, adjusted for age and gender | 5.8193 | 2.18E-19 |
| WAP4C, adjusted for age, gender, and BNP | 4.3416 | 4.52E-13 |

TABLE 17

Event: HF rehospitalization

| | Odds ratio (3rd vs 1st tertile) | P-value |
|---|---|---|
| WAP4C | 7.1342 | 4.30E-13 |
| WAP4C, adjusted for age and gender | 5.6849 | 8.12E-10 |
| WAP4C, adjusted for age, gender, and BNP | 3.5182 | 2.31E-05 |

TABLE 18

| Clinical dichotomy | AUC (confidence interval) | S.E. | P-value | N control | N disease |
|---|---|---|---|---|---|
| HF rehospitalization and/or all-cause death | 0.738 (0.706-0.770) | 0.016 | <0.001 | 607 | 374 |
| HF rehospitalization and/or all-cause death (T > 180 days) | 0.727 (0.694-0.760) | 0.017 | <0.001 | 607 | 345 |
| HF rehospitalization and/or all-cause death (T <= 180 days) | 0.797 (0.731-0.863) | 0.034 | <0.001 | 952 | 29 |
| HF rehospitalization | 0.732 (0.691-0.772) | 0.021 | <0.001 | 822 | 159 |
| HF rehospitalization (T > 180 days) | 0.720 (0.676-0.764) | 0.022 | <0.001 | 822 | 137 |
| HF rehospitalization (T <= 180 days) | 0.778 (0.700-0.857) | 0.04 | <0.001 | 959 | 22 |

TABLE 19

Event: HF rehospitalization

| Marker | AUC | 95% LCI | 95% UCI | SE | ND | D |
|---|---|---|---|---|---|---|
| BNP + WAP4C* | 0.814 | 0.780 | 0.848 | 0.017 | 822 | 159 |
| BNP | 0.798 | 0.761 | 0.835 | 0.019 | 822 | 159 |
| WAP4C | 0.732 | 0.691 | 0.772 | 0.021 | 822 | 159 |

TABLE 20

Event: all-cause death, MI, HF rehospitalization, stroke, or transient ischemic attack

| Marker | AUC | 95% LCI | 95% UCI | SE | ND | D |
|---|---|---|---|---|---|---|
| BNP + WAP4C* | 0.751 | 0.721 | 0.782 | 0.016 | 560 | 421 |
| WAP4C | 0.729 | 0.697 | 0.760 | 0.016 | 560 | 421 |
| BNP | 0.686 | 0.653 | 0.720 | 0.017 | 560 | 421 |

*Multiple logistic regression model

TABLE 21

Event: HF rehospitalization

| Comparison† | AUC difference | 95% LCI | 95% UCI | SE | p |
|---|---|---|---|---|---|
| BNP + WAP4C vs WAP4C | 0.082 | 0.042 | 0.122 | 0.021 | <0.0001 |
| BNP vs WAP4C | 0.066 | 0.018 | 0.114 | 0.025 | 0.0075 |
| BNP + WAP4C vs BNP | 0.016 | 0.004 | 0.028 | 0.006 | 0.0110 |

TABLE 22

Event: all-cause death, MI, HF rehospitalization, stroke, or transient ischemic attack

| Comparison† | AUC difference | 95% LCI | 95% UCI | SE | p |
|---|---|---|---|---|---|
| BNP + WAP4C vs BNP | 0.065 | 0.043 | 0.086 | 0.011 | <0.0001 |
| BNP + WAP4C vs WAP4C | 0.023 | 0.003 | 0.042 | 0.010 | 0.0218 |
| WAP4C vs BNP | 0.042 | 0.006 | 0.079 | 0.019 | 0.0226 |

†deLong, deLong, Clarke-Pearson method for contrast between pairs of ROC AUCs

One skilled in the art will readily appreciate that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of diagnosing heart failure in a subject, comprising:
    performing one or more assays selected from the group consisting of an assay that detects WAP four-disulfide core domain protein 2, an assay that detects ESAM, an assay that detects LTBR, an assay that detects Mesothelin, an assay that detects Syndecan-1, an assay that detects TROY, and an assay that detects PIGR on a body fluid sample obtained from said subject, thereby providing one or more assay result(s); and
    assigning a diagnosis that the subject has or does not have heart failure based on the assay result(s) obtained.

2. A method according to claim 1, further comprising performing one or more additional assay(s) selected from the group consisting of an assay that detects BNP, an assay that detects NT-proBNP, and an assay that detects proBNP on a body fluid sample obtained from said subject, thereby providing one or more additional assay result(s); and
    assigning a diagnosis that the subject has or does not have heart failure based on the assay result(s) obtained and on the additional assay result(s) obtained.

3. A method according to claim 1, wherein the assigning step comprises comparing each assay result obtained to a corresponding threshold level; and
    assigning an increased likelihood that the subject has heart failure when the assay result is greater than the threshold, relative to a risk assigned when the assay result is less than the threshold level, or by assigning a decreased likelihood that the subject has heart failure when the assay result is less than the threshold, relative to a risk assigned when the assay result is greater than the threshold level.

4. A method according to claim 1, wherein the threshold level is a level obtained from the subject at a time earlier than the time at which the body fluid sample used to provide the assay result was obtained.

5. A method according to claim 1, wherein the threshold level is determined from a first population of subjects suffering from heart failure, and the threshold level is selected to separate said population from a second population not suffering from heart failure.

6. A method according to claim 3, wherein the threshold level separates said first population from said second population with an odds ratio of at least 2 or more or 0.5 or less.

7. A method according to claim 3, wherein the threshold level separates said first population from said second population with an odds ratio of at least 3 or more or 0.33 or less.

8. A method according to claim 1, wherein the body fluid sample is selected from the group consisting of urine, blood, serum, and plasma.

9. A method according to claim 1, wherein the subject has a measured level of BNP, NTproBNP, or proBNP which is not indicative of a heart failure diagnosis.

10. A method according to claim 1, wherein the subject is not exhibiting symptomatic heart failure.

11. A method of assigning one or more of a mortality risk due to cardiovascular disease, a risk of myocardial infarction, a risk of rehospitalization due to heart failure, a risk of stroke, or a risk of a transient ischemic attack to a subject having clinically apparent coronary heart disease, comprising:
    performing one or more assays selected from the group consisting of an assay that detects WAP four-disulfide core domain protein 2, an assay that detects ESAM, an assay that detects LTBR, an assay that detects Mesothelin, an assay that detects Syndecan-1, an assay that detects TROY, and an assay that detects PIGR on a body fluid sample obtained from said subject, thereby providing one or more assay result(s); and
    assigning the risk to the subject based on the assay result(s) obtained.

12. A method according to claim 11, further comprising performing one or more additional assay(s) selected from the group consisting of an assay that detects BNP, an assay that detects NT-proBNP, and an assay that detects proBNP on a body fluid sample obtained from said subject, thereby providing one or more additional assay result(s); and assigning a mortality risk to the subject based on the assay result(s) obtained and on the additional assay result(s) obtained.

13. A method according to claim 11, wherein the assigning step comprises comparing each assay result obtained to a corresponding threshold level; and
assigning an increased mortality risk to the subject when the assay result is greater than the threshold, relative to a risk assigned when the assay result is less than the threshold level, or by assigning a decreased mortality risk to the subject when the assay result is less than the threshold, relative to a risk assigned when the assay result is greater than the threshold level.

14. A method according to claim 11, wherein the threshold level is a level obtained from the subject at a time earlier than the time at which the body fluid sample used to provide the assay result was obtained.

15. A method according to claim 11, wherein the threshold level is determined from a first population of subjects suffering from heart failure, and the threshold level is selected to separate said population from a second population not suffering from heart failure.

16. A method according to claim 13, wherein the threshold level separates said first population from said second population with an odds ratio of at least 2 or more or 0.5 or less.

17. A method according to claim 13, wherein the threshold level separates said first population from said second population with an odds ratio of at least 3 or more or 0.33 or less.

18. A method according to claim 11, wherein the body fluid sample is selected from the group consisting of urine, blood, serum, and plasma.

19. A method of assigning one or more of a mortality risk due to cardiovascular disease, a risk of myocardial infarction, a risk of rehospitalization due to heart failure, a risk of stroke, or a risk of a transient ischemic attack to a subject having clinically apparent heart failure, comprising:
performing one or more assays selected from the group consisting of an assay that detects WAP four-disulfide core domain protein 2, an assay that detects ESAM, an assay that detects LTBR, an assay that detects Mesothelin, an assay that detects Syndecan-1, an assay that detects TROY, and an assay that detects PIGR on a body fluid sample obtained from said subject, thereby providing one or more assay result(s); and
assigning the risk to the subject based on the assay result(s) obtained.

20. A method according to claim 19, further comprising performing one or more additional assay(s) selected from the group consisting of an assay that detects BNP, an assay that detects NT-proBNP, and an assay that detects proBNP on a body fluid sample obtained from said subject, thereby providing one or more additional assay result(s); and
assigning a mortality risk to the subject based on the assay result(s) obtained and on the additional assay result(s) obtained.

21. A method according to claim 19, wherein the assigning step comprises comparing each assay result obtained to a corresponding threshold level; and
assigning an increased mortality risk to the subject when the assay result is greater than the threshold, relative to a risk assigned when the assay result is less than the threshold level, or by assigning a decreased mortality risk to the subject when the assay result is less than the threshold, relative to a risk assigned when the assay result is greater than the threshold level.

22. A method according to claim 19, wherein the threshold level is a level obtained from the subject at a time earlier than the time at which the body fluid sample used to provide the assay result was obtained.

23. A method according to claim 19, wherein the threshold level is determined from a first population of subjects suffering from heart failure, and the threshold level is selected to separate said population from a second population not suffering from heart failure.

24. A method according to claim 21, wherein the threshold level separates said first population from said second population with an odds ratio of at least 2 or more or 0.5 or less.

25. A method according to claim 21, wherein the threshold level separates said first population from said second population with an odds ratio of at least 3 or more or 0.33 or less.

26. A method according to claim 19, wherein the body fluid sample is selected from the group consisting of urine, blood, serum, and plasma.

* * * * *

SEQUENCE LISTING

<160> NUMBER OF SEQ ID NOS: 13

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65              70                  75                  80

Val Gln Gly Ser Gly Cys Phe Gly Arg Lys Met Asp Arg Ile Ser Ser
            85                  90                  95

Ser Ser Gly Leu Gly Cys Lys Val Leu Arg Arg His
            100                 105

<210> SEQ ID NO 2
<211> LENGTH: 134
<212> TYPE: PRT
<213> ORGANISM: Homo sapiens

<400> SEQUENCE: 2

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65              70                  75                  80

Glu Val Ala Thr Glu Gly Ile Arg Gly His Arg Lys Met Val Leu Tyr
            85                  90                  95

Thr Leu Arg Ala Pro Arg Ser Pro Lys Met Val Gln Gly Ser Gly Cys
        100                 105                 110

Phe Gly Arg Lys Met Asp Arg Ile Ser Ser Ser Ser Gly Leu Gly Cys
    115                 120                 125

Lys Val Leu Arg Arg His
    130

<210> SEQ ID NO 3
<211> LENGTH: 390
<212> TYPE: PRT
<213> ORGANISM: Homo sapiens

<400> SEQUENCE: 3

Met Ile Ser Leu Pro Gly Pro Leu Val Thr Asn Leu Leu Arg Phe Leu
1               5                   10                  15

Phe Leu Gly Leu Ser Ala Leu Ala Pro Pro Ser Arg Ala Gln Leu Gln
            20                  25                  30

Leu His Leu Pro Ala Asn Arg Leu Gln Ala Val Glu Gly Gly Glu Val
        35                  40                  45

Val Leu Pro Ala Trp Tyr Thr Leu His Gly Glu Val Ser Ser Ser Gln
    50                  55                  60

```
Pro Trp Glu Val Pro Phe Val Met Trp Phe Lys Gln Lys Glu Lys
 65                  70                  75                  80

Glu Asp Gln Val Leu Ser Tyr Ile Asn Gly Val Thr Thr Ser Lys Pro
             85                  90                  95

Gly Val Ser Leu Val Tyr Ser Met Pro Ser Arg Asn Leu Ser Leu Arg
            100                 105                 110

Leu Glu Gly Leu Gln Glu Lys Asp Ser Gly Pro Tyr Ser Cys Ser Val
        115                 120                 125

Asn Val Gln Asp Lys Gln Gly Lys Ser Arg Gly His Ser Ile Lys Thr
    130                 135                 140

Leu Glu Leu Asn Val Leu Val Pro Pro Ala Pro Pro Ser Cys Arg Leu
145                 150                 155                 160

Gln Gly Val Pro His Val Gly Ala Asn Val Thr Leu Ser Cys Gln Ser
                165                 170                 175

Pro Arg Ser Lys Pro Ala Val Gln Tyr Gln Trp Asp Arg Gln Leu Pro
            180                 185                 190

Ser Phe Gln Thr Phe Phe Ala Pro Ala Leu Asp Val Ile Arg Gly Ser
        195                 200                 205

Leu Ser Leu Thr Asn Leu Ser Ser Ser Met Ala Gly Val Tyr Val Cys
    210                 215                 220

Lys Ala His Asn Glu Val Gly Thr Ala Gln Cys Asn Val Thr Leu Glu
225                 230                 235                 240

Val Ser Thr Gly Pro Gly Ala Ala Val Val Ala Gly Ala Val Val Gly
                245                 250                 255

Thr Leu Val Gly Leu Gly Leu Leu Ala Gly Leu Val Leu Leu Tyr His
            260                 265                 270

Arg Arg Gly Lys Ala Leu Glu Glu Pro Ala Asn Asp Ile Lys Glu Asp
        275                 280                 285

Ala Ile Ala Pro Arg Thr Leu Pro Trp Pro Lys Ser Ser Asp Thr Ile
    290                 295                 300

Ser Lys Asn Gly Thr Leu Ser Ser Val Thr Ser Ala Arg Ala Leu Arg
305                 310                 315                 320

Pro Pro His Gly Pro Pro Arg Pro Gly Ala Leu Thr Pro Thr Pro Ser
                325                 330                 335

Leu Ser Ser Gln Ala Leu Pro Ser Pro Arg Leu Pro Thr Thr Asp Gly
            340                 345                 350

Ala His Pro Gln Pro Ile Ser Pro Ile Pro Gly Gly Val Ser Ser Ser
        355                 360                 365

Gly Leu Ser Arg Met Gly Ala Val Pro Val Met Val Pro Ala Gln Ser
    370                 375                 380

Gln Ala Gly Ser Leu Val
385                 390

<210> SEQ ID NO 4
<211> LENGTH: 435
<212> TYPE: PRT
<213> ORGANISM: Homo sapiens

<400> SEQUENCE: 4

Met Leu Leu Pro Trp Ala Thr Ser Ala Pro Gly Leu Ala Trp Gly Pro
 1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45
```

```
Glu Tyr Tyr Glu Pro Gln His Arg Ile Cys Cys Ser Arg Cys Pro Pro
     50                  55                  60

Gly Thr Tyr Val Ser Ala Lys Cys Ser Arg Ile Arg Asp Thr Val Cys
 65                  70                  75                  80

Ala Thr Cys Ala Glu Asn Ser Tyr Asn Glu His Trp Asn Tyr Leu Thr
                     85                  90                  95

Ile Cys Gln Leu Cys Arg Pro Cys Asp Pro Val Met Gly Leu Glu Glu
                100                 105                 110

Ile Ala Pro Cys Thr Ser Lys Arg Lys Thr Gln Cys Arg Cys Gln Pro
            115                 120                 125

Gly Met Phe Cys Ala Ala Trp Ala Leu Glu Cys Thr His Cys Glu Leu
        130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365

Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
    435

<210> SEQ ID NO 5
<211> LENGTH: 630
```

<212> TYPE: PRT
<213> ORGANISM: Homo sapiens

<400> SEQUENCE: 5

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
        530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 6
<211> LENGTH: 64
<212> TYPE: PRT
<213> ORGANISM: Homo sapiens

<400> SEQUENCE: 6

Val Gln Gly Gly Arg Gly Gly Gln Ala Arg Ala Gly Arg Ala Gly
1               5                   10                  15

Gly Val Glu Val Gly Ala Leu Ser His Pro Ser Leu Cys Arg Gly Pro
            20                  25                  30

Leu Gly Asp Ala Leu Pro Pro Arg Thr Trp Thr Cys Ser His Arg Pro
        35                  40                  45

Gly Thr Ala Pro Ser Leu His Pro Gly Leu Arg Ala Pro Leu Pro Cys
    50                  55                  60

<210> SEQ ID NO 7
<211> LENGTH: 310
<212> TYPE: PRT
<213> ORGANISM: Homo sapiens

<400> SEQUENCE: 7

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

```
Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
                100                 105                 110

Gly Leu Thr Ala Arg Glu Gln Ala Thr Pro Arg Pro Arg Glu Thr
                115                 120                 125

Thr Gln Leu Pro Thr Thr His Leu Ala Ser Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
                180                 185                 190

Glu Asp Gly Ala Ser Ser Gln Leu Pro Ala Ala Glu Gly Ser Gly Glu
                195                 200                 205

Gln Asp Phe Thr Phe Glu Thr Ser Gly Glu Asn Thr Ala Val Val Ala
        210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
                260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
        290                 295                 300

Gln Glu Glu Phe Tyr Ala
305                 310

<210> SEQ ID NO 8
<211> LENGTH: 310
<212> TYPE: PRT
<213> ORGANISM: Homo sapiens

<400> SEQUENCE: 8

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
```

```
                    85                  90                  95
Glu Gly Pro Lys Glu Gly Glu Ala Val Val Leu Pro Glu Val Glu Pro
                100                 105                 110

Gly Leu Thr Ala Arg Glu Gln Glu Ala Thr Pro Arg Pro Arg Glu Thr
            115                 120                 125

Thr Gln Leu Pro Thr Thr His Leu Ala Ser Thr Thr Thr Ala Thr Thr
        130                 135                 140

Ala Gln Glu Pro Ala Thr Ser His Pro His Arg Asp Met Gln Pro Gly
    145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 9
<211> LENGTH: 764
<212> TYPE: PRT
<213> ORGANISM: Homo sapiens

<400> SEQUENCE: 9

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
                20                  25                  30

Gly Asn Ser Val Ser Ile Thr Cys Tyr Tyr Pro Pro Thr Ser Val Asn
            35                  40                  45

Arg His Thr Arg Lys Tyr Trp Cys Arg Gln Gly Ala Arg Gly Gly Cys
        50                  55                  60

Ile Thr Leu Ile Ser Ser Glu Gly Tyr Val Ser Ser Lys Tyr Ala Gly
    65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140
```

```
Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
            165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
            195                 200                 205

Gln Leu Arg Leu Ser Asp Ala Gly Gln Tyr Leu Cys Gln Ala Gly Asp
            210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
            245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Asn Thr Leu Gly Lys
            275                 280                 285

Arg Ala Pro Ala Phe Glu Gly Arg Ile Leu Leu Asn Pro Gln Asp Lys
290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
            325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
            355                 360                 365

Val Leu Cys Pro Tyr Asn Arg Lys Glu Ser Lys Ser Ile Lys Tyr Trp
            370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
            405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
            435                 440                 445

Trp Arg Thr Thr Val Glu Ile Lys Ile Ile Glu Gly Glu Pro Asn Leu
450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
            485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
            515                 520                 525

Leu Thr Leu Asn Leu Val Thr Arg Ala Asp Glu Gly Trp Tyr Trp Cys
            530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
```

```
                    565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
    755                 760

<210> SEQ ID NO 10
<211> LENGTH: 120
<212> TYPE: PRT
<213> ORGANISM: Homo sapiens

<400> SEQUENCE: 10

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val
        115                 120

<210> SEQ ID NO 11
<211> LENGTH: 22
<212> TYPE: PRT
<213> ORGANISM: Homo sapiens

<400> SEQUENCE: 11

Leu Gln Val Gln Val Asn Leu Pro Val Ser Pro Leu Pro Thr Tyr Pro
```

```
                            -continued
1               5                   10                  15
Tyr Ser Phe Phe Tyr Pro
                        20

<210> SEQ ID NO 12
<211> LENGTH: 10
<212> TYPE: PRT
<213> ORGANISM: Homo sapiens

<400> SEQUENCE: 12

Leu Leu Cys Pro Asn Gly Gln Leu Ala Glu
1               5                   10

<210> SEQ ID NO 13
<211> LENGTH: 28
<212> TYPE: PRT
<213> ORGANISM: Homo sapiens

<400> SEQUENCE: 13

Ala Leu Phe His Trp His Leu Lys Thr Arg Arg Leu Trp Glu Ile Ser
1               5                   10                  15

Gly Pro Arg Pro Arg Arg Pro Thr Trp Asp Ser Ser
                20                  25
```